(12) United States Patent
Emblidge et al.

(10) Patent No.: US 6,620,980 B1
(45) Date of Patent: Sep. 16, 2003

(54) METHOD FOR RECOVERY OF PHENOL FROM AQUEOUS STREAMS

(75) Inventors: Robert W. Emblidge, Swarthmore, PA (US); Scott R. Keenan, Marlton, NJ (US)

(73) Assignee: Sunoco Inc (R&M), Philadelphia, PA (US)

( * ) Notice: Subject to any disclaimer, the term of this patent is extended or adjusted under 35 U.S.C. 154(b) by 0 days.

(21) Appl. No.: 10/121,996

(22) Filed: Apr. 12, 2002

(51) Int. Cl.[7] .................................................. C07L 37/68
(52) U.S. Cl. ....................................................... 568/754
(58) Field of Search ......................................... 568/754

(56) References Cited

U.S. PATENT DOCUMENTS

| 2,734,085 A | * | 2/1956 | Adams |
| 2,812,305 A | * | 11/1957 | Manka |
| 3,467,721 A | * | 9/1969 | Bewley |
| 3,963,610 A | * | 6/1976 | Hauschulz |
| 4,026,791 A | * | 5/1977 | Wallace |
| 4,626,600 A | * | 12/1986 | Flumer |
| 5,338,453 A | * | 8/1994 | Fraini |
| 5,510,543 A | * | 4/1996 | Fulmer |
| 5,811,598 A | * | 9/1998 | Alessi |
| 2001/0000260 A1 | * | 4/2001 | Taggart |

FOREIGN PATENT DOCUMENTS

EP          85289         *  8/1983

* cited by examiner

*Primary Examiner*—Michael L. Shippen
(74) *Attorney, Agent, or Firm*—Robert A. Koons, Jr.; Matthew P. McWilliams; Buchanan Ingersoll, PC

(57) ABSTRACT

An improved method for the recovery of phenol from aqueous streams comprises adding a relatively non-polar solvent to a phenol containing aqueous stream to improve the separation of the phenol form the aqueous stream. The improvement results in a phenol stream with a reduced level of salt carried over from the aqueous stream.

5 Claims, No Drawings

METHOD FOR RECOVERY OF PHENOL FROM AQUEOUS STREAMS

FIELD OF THE INVENTION

The invention is drawn generally to the field of the manufacture of phenol. Specifically, the invention is drawn to a method for the recovery of phenol from an aqueous stream, wherein the phenol is partitioned from the aqueous stream in such a way as to minimize the water and salt content of the phenol.

BACKGROUND OF THE INVENTION

It is very common in the manufacture of phenol to generate aqueous streams containing significant amounts of phenol either as the free phenol or as a phenate salt. In order to maximize yield and minimize the environmental impact of waste water streams, manufacturers undertake to recover as much of this phenol as possible. The recovered phenol is generally placed back into the process stream for further refining. Phenol containing aqueous streams are generated from a number of sources in a phenol manufacturing facility. A primary source of these streams is from the recovery of phenol from non-phenol organic streams such as cumene and alpha-methylstyrene. The phenol is removed from these organic streams by extraction with an aqueous base such as sodium hydroxide to form an aqueous phenate solution. The phenol is subsequently sprung from the aqueous solution by neutralization with an appropriate acid. The sprung phenol is then separated from the aqueous layer and recycled to crude phenol processing.

A drawback of adding phenol recovered in this fashion to a process stream is that the recovered phenol generally contains a substantial amount of water and dissolved salts carried over from the aqueous streams. The salts may subsequently precipitate in process equipment, causing damage and lengthy shutdowns for cleaning and repairs.

It would therefore be desirable to provide a method for recovering phenol from salt containing aqueous streams that minimizes the quantity of water and dissolved salts carried over into the recovered phenol.

SUMMARY OF THE INVENTION

The present invention provides a method for minimizing the content of salt in phenol recovered from salt containing aqueous streams. The method of the present invention makes use of relatively non-polar solvents to improve the separation between phenol and salt containing water solutions. Preferred non-polar solvents are organic streams comprising cumene, alpha-methylstyrene or mixtures thereof due to their ready availability in a phenol manufacturing environment.

By adding a relatively non-polar solvent to a water/phenol mixture prior to separation, the affinity of water for the phenol containing organic layer is reduced. By reducing the affinity of water for the organic layer, the quantity of salt carried into the organic layer is minimized. Further, addition of a relatively non-polar solvent reduces the affinity of phenol for the aqueous phase. Thus the method according to the current invention provides a phenol stream with a substantially reduced salt content. Since any non-polar solvent added to affect the separation must be removed in further processing, care must be taken to minimize the quantity of non-polar solvent added to minimize the further costs of processing the recovered material.

DETAILED DESCRIPTION OF THE INVENTION

In the process according to the current invention phenol with a low salt content is recovered from a salt containing aqueous stream. The low salt content in the recovered phenol is accomplished by addition of a relatively non-polar solvent to the phenol containing aqueous stream prior to separation. By relatively non-polar as referred to herein is meant non-polar relative to phenol and water.

The process according to the current invention is applicable to process streams comprising water and phenol. In the preferred embodiment, an aqueous process stream is generated by extraction of phenol from an organic stream with an aqueous base such as sodium hydroxide to form an aqueous phenate solution. The phenol is subsequently sprung from the phenate solution by neutralization with an appropriate acid. Prior to separation of the sprung phenol from the aqueous phase, a relatively non-polar solvent is added to the phenol water mixture. The combined mixture is then agitated to effect mixing of the phenol and non-polar solvent. The combined mixture is then separated into a phenol containing organic layer and a waste aqueous layer. Preferred solvents are organic streams comprising cumene, alpha-methylstyrene or mixtures thereof due to their ready availability in a phenol manufacturing plant. The organic streams utilized will generally comprise crude streams of cumene, alpha-methylstyrene or mixtures thereof that have been previously isolated from the decomposition of cumene hydroperoxide in the production of phenol. These streams will therefore very often contain minor amounts of other components. The exact composition of these streams is not critical to the functioning of the method according to the current invention. Rather, it is only important that the solvent composition used be as a whole non-polar relative to water and phenol. Preferably, the relatively non-polar solvent is added in a ratio to phenol of about 0.4:1 to about 1.2:1. More preferably the ratio of non-polar solvent to phenol is about 0.5:1 to about 1:1.

EXAMPLES

A number of examples were run using a typical mixture containing an oil and a salt containing aqueous solution. The oil used comprised primarily phenol (approximately 79.25%), approximately 18.4 percent water, as determined by Karl Fisher analysis, 0.2 percent salt, and minor amounts of other cumene hydroperoxide decomposition products, such as acetone and alpha-methylstyrene. This oil was mixed with an aqueous stream containing approximately 17.9 percent salt, as determined by ash. The oil and water were mixed in proportions from about 1:1 oil/water to about 1:4 oil/water. Various amounts of cumene were added to the mixed oil/water and the samples were heated with agitation to mimic plant conditions. The composition of mixtures and the quantity of cumene added in each example are shown in Table 1. The weight of water reported in column 3 for each example does not include the water content in the base oil sample. In the baseline sample, no cumene was added to the mixture prior to separation.

TABLE 1

| Trial | wt. oil in mixture (g) | wt. water in mixture (g) | wt. cumene added (g) | wt. organic recovered oil + cumene (g) | wt. water recovered (g) | % recovery organic oil + cumene | % water recovery | % recovery of phenol |
|---|---|---|---|---|---|---|---|---|
| baseline | 52.39 | 58.33 | 0.00 | 51.43 | 57.28 | 98.17 | 98.20 | 97.78 |
| 1 | 52.20 | 58.08 | 0.35 | 51.83 | 56.92 | 98.63 | 98.00 | 99.56 |
| 2 | 52.62 | 57.85 | 0.87 | 51.90 | 57.55 | 97.03 | 99.48 | 97.89 |
| 3 | 53.46 | 58.18 | 2.34 | 52.39 | 58.67 | 93.89 | 100.84 | 96.44 |
| 4 | 52.29 | 57.77 | 4.48 | 53.61 | 59.08 | 94.43 | 102.27 | 99.20 |
| 5 | 52.31 | 57.58 | 8.84 | 56.88 | 59.96 | 93.02 | 104.13 | 101.25 |
| 6 | 20.16 | 103.26 | 1.88 | 19.69 | 103.68 | 89.34 | 100.41 | 95.06 |
| 7 | 20.17 | 103.70 | 3.69 | 21.07 | 104.59 | 88.31 | 100.86 | 97.93 |
| 8 | 20.55 | 105.06 | 8.41 | 26.26 | 105.52 | 90.68 | 100.44 | 93.92 |
| 9 | 20.59 | 104.57 | 16.78 | 34.15 | 105.52 | 91.38 | 100.91 | 95.47 |

The mixtures in each example were separated into organic and aqueous layers, which were then analyzed for salt content. The organic layers were also analyzed by gas chromatography and for water by Karl Fisher analysis. The results are shown in Table 2.

TABLE 2

| Trial | wt. of salt in recovered organic (g) | wt. percent of salt in recovered organic | percent water content of recovered organic by KF | wt. of salt in recovered water (g) | wt. percent of salt in recovered water | percent of total salt in recovered organic | percent of total salt in recovered water |
|---|---|---|---|---|---|---|---|
| baseline | 0.09 | 0.19 | 18.8 | 10.51 | 18.35 | 0.85% | 99.15% |
| 1 | 0.08 | 0.16 | 17.6 | 10.22 | 17.96 | 0.77% | 99.23% |
| 2 | 0.11 | 0.20 | 17.6 | 10.22 | 17.76 | 1.06% | 98.94% |
| 3 | 0.09 | 0.17 | 16.1 | 10.23 | 17.43 | 0.87% | 99.13% |
| 4 | 0.08 | 0.15 | 14.1 | 10.07 | 17.05 | 0.79% | 99.21% |
| 5 | 0.05 | 0.09 | 12.9 | 10.00 | 16.68 | 0.50% | 99.50% |
| 6 | 0.02 | 0.11 | 13.8 | 16.93 | 16.33 | 0.12% | 99.88% |
| 7 | 0.01 | 0.04 | 12.4 | 16.97 | 16.23 | 0.06% | 99.94% |
| 8 | 0.00 | 0.01 | 7.6 | — | — | ~0% | ~100% |
| 9 | 0.00 | 0.01 | 4.9 | — | — | ~0% | ~100% |

As can be seen from the data in Table 2, the concentration of water and salt in the recovered organic phase began to drop precipitously as the ratio of cumene added to phenol in the oil mixture approached about 0.1:1, trial 6. Where the ratio of cumene added to phenol in the oil mixture approached about 0.5:1, trial 8, the amount of residual salt in the recovered organic layer approached zero. Referring to the last three columns of Table 1, it can be seen that while the total recovery of the combined oil and cumene dropped as the quantity of cumene added increased, the recovery of phenol remained relatively constant. The drop in the overall recovery of the combined oil and cumene is consistent with the precipitous drop in the water content of the recovered organic phase with increasing cumene. The 4.9 percent water content in the recovered organic phase in trial 9 is significantly less than the 18.4 percent content in the oil prior to mixing and separation. This difference accounts almost entirely for the reduced overall recovery of the oil/cumene phase.

Comparing trials 8 and 9, it can be seen that adding additional cumene beyond a ratio to phenol of about 0.5:1 does not adversely affect the recovery of phenol or the salt content of the recovered phenol. However, since any solvent that is added to the phenol in the recovery process must be subsequently removed by distillation, it is preferable to add as little solvent as is necessary to affect a good separation with low residual salt in the recovered phenol.

The examples disclosed herein demonstrate an embodiment of the invention drawn to recovery of phenol from an aqueous stream generated by neutralization of an alkali phenate solution. However, those familiar with the production of phenol will recognize that the invention disclosed is not limited to this embodiment. The method of the present invention may be used with a number of phenol containing aqueous streams to maximize recovery of phenol and minimize the water and salt content of said phenol. Further, although organic streams comprising cumene, alpha-methylstyrene and mixtures thereof are preferred as the relatively non-polar solvent in the present invention, it will be recognized that any solvent composition that is non-polar relative to phenol and water will be useful in the current invention. The scope of the present invention will be apparent from the claims appended hereto.

What is claimed is:

1. A method of reducing the salt content of phenol recovered from an aqueous alkali phenate stream, said method comprising:
   a) adding an acid to said aqueous alkali phenate stream to produce a two-phase composition comprising a phenol containing organic phase and a salt containing water phase,
   b) adding a non-polar solvent to said composition wherein the weight ratio of said non-polar solvent added to phenol is from about 0.5:1 to about 1.2:1,
   c) agitating said composition at a temperature of approximately 30° C. to 60° C., and
   d) separating said composition into a salt containing water layer and a phenol containing organic layer, whereby 90 percent or more of said salt is carried into the salt containing water layer.

2. The method of claim 1, wherein said non-polar solvent comprises an organic solvent selected from the group consisting of cumene, alpha-methylstyrene and mixtures thereof.

3. The method of claim 1, wherein the salt content of said phenol containing organic layer is less than about 100 ppm.

4. The method according to claim 1, wherein the salt content of said salt containing water phase is about 15% to about 25%.

5. The method of claim 1, wherein said aqueous alkali phenate stream is generated by extraction of a phenol containing organic stream with an aqueous alkali hydroxide.

* * * * *